(12) United States Patent
Dailey et al.

(10) Patent No.: US 7,358,499 B2
(45) Date of Patent: Apr. 15, 2008

(54) LASER ALIGNMENT SYSTEM FOR NUCLEAR MEDICAL DETECTOR

(75) Inventors: George William Dailey, Glen Ellyn, IL (US); Grant Albert, Elgin, IL (US); Matthew Freeman, Cary, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 166 days.

(21) Appl. No.: 11/455,623

(22) Filed: Jun. 19, 2006

(65) Prior Publication Data

US 2007/0007456 A1 Jan. 11, 2007

Related U.S. Application Data

(60) Provisional application No. 60/691,855, filed on Jun. 17, 2005.

(51) Int. Cl.
*G01T 1/166* (2006.01)
(52) U.S. Cl. .................................. 250/363.05
(58) Field of Classification Search ........... 250/363.05; 378/20, 206
See application file for complete search history.

(56) References Cited

U.S. PATENT DOCUMENTS 6,878,941 B2 * 4/2005 Balan et al. ........... 250/363.02
6,917,666 B2 * 7/2005 Wollenweber ............... 378/20

* cited by examiner

*Primary Examiner*—Constantine Hannaher (57) ABSTRACT

An alignment system for use in connection with a patient handling system and a nuclear medicine gantry is provided. The alignment system includes a nuclear camera alignment fixture mountable to the nuclear detector. The nuclear camera alignment fixture includes a pair of lasers mounted in a known position relative to a center of the nuclear detector and oriented substantially toward the nuclear medicine gantry. The nuclear camera alignment fixture further includes a pair of laser targets provided on the nuclear medicine gantry. Each laser target has a fixed location with respect to an axis of rotation of the nuclear medicine gantry. The nuclear detector is moved relative to the nuclear medicine gantry until a laser beam from each laser hits a respective laser target. The alignment system is also capable of aligning the patient handling system with respect to the axis of rotation of the nuclear medicine gantry.

19 Claims, 11 Drawing Sheets

LASER ALIGNMENT SYSTEM FOR NUCLEAR MEDICAL DETECTOR

CROSS-REFERENCE TO RELATED APPLICATION

The present application claims the benefit of and priority to U.S. Provisional Application Ser. No. 60/691,855, filed on Jun. 17, 2005, the entire content of which is incorporated herein by reference.

BACKGROUND

1. Technical Field

The present disclosure relates to the field of gamma detectors used in the area of nuclear medicine and, more particularly to alignment systems including laser alignment systems for nuclear medical detectors and nuclear medicine imaging systems.

2. Background of Related Art

Nuclear or scintillation detectors (also called gamma cameras) are responsive to radiation emitted from a radiopharmaceutical injected into a patient during an imaging study. A radiopharmaceutical is typically selected that will target a particular organ or tissue of interest. In computed tomography studies, a detector head (or pair of heads) revolves around the patient and collects the emissions at various angles in order to generate an image of the targeted organ or tissue. In total body studies, the detectors may translate at a fixed or variable altitude along the patient.

A common problem in nuclear medicine imaging systems is the inaccurate alignment of the nuclear detector to the detector axis of rotation. Moreover, another common problem is the alignment of the patient bed or patient handling system, while in or out of axis, with the axis of rotation of the nuclear camera. Prior to the use and/or operation of the nuclear medicine imaging system, it is important that the nuclear detectors and the patient handling system be accurately and properly aligned with the ring of a nuclear medicine gantry.

Accordingly, a need exists for decreasing the inaccuracies in the alignment of the nuclear detector to the axis of rotation thereof and in the alignment of the patient bed with the axis of rotation of the nuclear detector.

SUMMARY

The present disclosure relates to alignment systems including laser alignment systems for nuclear medical detectors and nuclear medicine imaging systems.

In accordance with an aspect of the present disclosure, an alignment system for use in connection with at least one of a patient handling system, and a nuclear medicine gantry defining an axis of rotation and having a nuclear detector operatively mounted thereto is provided. The alignment system includes a nuclear camera alignment fixture selectively fixedly mountable to a face of the nuclear detector. The nuclear camera alignment fixture includes a pair of lasers oriented substantially toward the nuclear medicine gantry. Each laser is capable of emitting a respective laser beam therefrom. The nuclear detector includes a pair of laser targets provided on the nuclear medicine gantry. Each laser target has a fixed location with respect to the axis of rotation of the nuclear medicine gantry. The nuclear detector is moved relative to the nuclear medicine gantry until each laser beam hits a respective laser target.

The pair of lasers may be divergent from one another. The nuclear camera alignment fixture may include a plate selectively mountable to the face of the nuclear detector utilizing the same registration points as the detector's collimator. Each laser may be mounted to the plate thereof. The lasers may be magnetically mounted to the plate. The lasers may be oriented to transmit laser beams in a divergent direction relative to one another.

The alignment system may further include a patient handling system alignment assembly including a first and a second front patient handling system alignment fixture each selectively mountable to the patient handling system; a rear patient handling system alignment fixture selectively mountable to a mounting platform of the nuclear medicine gantry; and a laser supported on the first front patient handling system alignment fixture and oriented to emit a laser beam in the direction of the nuclear medicine gantry. In operation, a height of the patient handling system may be adjusted until the laser beam of the first front patient handling system alignment fixture hits a target of the rear patient handling system alignment fixture.

The first front patient handling system alignment fixture may be mounted to the patient handling system at a location remote from the nuclear medicine gantry. The second front patient handling system alignment fixture may be mounted to the patient handling system at a location proximate to the nuclear medicine gantry. The second front patient handling system alignment fixture may include a target supported thereon. Accordingly, the laser beam emitted by the laser of the first front patient handling system may be directed through the target of the second front patient handling system alignment fixture.

The rear patient handling system alignment fixture may include a pair of uprights extending therefrom. A first of the pair of uprights may include an aperture through which the laser beam emitted by the laser of the first front patient handling system is directed through and a second of the pair of uprights may include a target.

The alignment system may further include a pair of uprights mounted to the nuclear camera alignment fixture. Each upright of the nuclear camera alignment fixture may include an aperture formed near a distal end thereof. The laser beam emitted by the laser of the first front patient handling system may be directed through each of the apertures of the pair of uprights of the nuclear camera alignment fixture.

The patient handling system may be adjusted such that the laser beam emitted by the laser of the first front patient handling system is directed through each of the apertures of the pair of uprights of the nuclear camera alignment fixture. The pair of uprights of the nuclear camera alignment fixture may be in a plane defined by the axis of rotation of the nuclear medicine gantry.

The nuclear camera alignment fixture may include a plate selectively mountable to the face of the nuclear detector. Each of the pair of lasers may be mounted to the plate thereof. Each of the pair of lasers of the nuclear camera alignment fixture may be magnetically mounted to the plate thereof. Each of the pair of lasers of the nuclear camera alignment fixture may be oriented to transmit laser beams in a divergent direction relative to one another.

According to another aspect of the present disclosure, an alignment system for use in connection with at least one of a patient handling system, and a nuclear medicine gantry defining an axis of rotation and having a nuclear detector operatively mounted thereto is provided. The alignment system includes a nuclear camera alignment fixture selectively fixedly mountable to a face of the nuclear detector. The nuclear camera alignment fixture includes a pair of lasers oriented substantially toward the nuclear medicine gantry. Each laser is capable of emitting a respective laser beam therefrom. A pair of laser targets is provided on the nuclear medicine gantry. Each laser target has a fixed location with respect to the axis of rotation of the nuclear medicine gantry. In operation, the nuclear detector is moved relative to the nuclear medicine gantry until each laser beam hits a respective laser target which resides on the nuclear medicine gantry which in turn defines the axis of rotation.

The alignment system further includes a patient handling system alignment assembly having a first and a second front patient handling system alignment fixture each selectively mountable to the patient handling system; a rear patient handling system alignment fixture selectively mountable to a mounting platform of the nuclear medicine gantry; and a laser supported on the first front patient handling system alignment fixture and oriented to emit a laser beam in the direction of the nuclear medicine gantry. In operation, a height of the patient handling system is adjusted until the laser beam of the first front patient handling system alignment fixture hits a target of the rear patient handling system alignment fixture.

According to a further aspect of the present disclosure a method of aligning a nuclear detector of a nuclear medicine gantry and a patient handling system each to an axis of rotation of the nuclear medicine gantry is provided. The method includes the steps of mounting a pair of lasers to the nuclear detector, wherein the pair of lasers are substantially directed toward the nuclear medicine gantry; emitting laser beams from each of the pair of lasers in the direction of the nuclear medicine gantry; moving the nuclear detector relative to a ring of the nuclear medicine gantry until each laser beam hits a respective target provided on the nuclear medicine gantry, wherein each target is located at a known position relative to the axis of rotation of the nuclear medicine gantry; mounting a laser to the patient handling system, wherein the laser of the patient handling system is directed toward the nuclear medicine gantry; emitting a laser beam from the laser of the patient handling system in the direction of the nuclear medicine gantry; and moving the patient handling system until the laser beam thereof is aligned with the axis of rotation of the nuclear medicine gantry.

It is contemplated that the pair of lasers may be divergent from one another.

The method may further include the step of emitting the laser beam of the laser of the patient handling system through at least one upright provided on the nuclear detector.

The method may still further include the steps of placing the laser of the patient handling system at a location remote relative to the nuclear medicine gantry; and emitting the laser beam of the laser of the patient handling system through a target provided on the patient handling system at a location in close proximity to the nuclear medicine gantry.

BRIEF DESCRIPTION OF THE DRAWINGS

The invention may take physical form in certain parts and arrangements of parts, a preferred embodiment of which will be described in detail herein and illustrated in the accompanying drawings which form a part hereof and wherein.

DETAILED DESCRIPTION OF EMBODIMENTS

The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
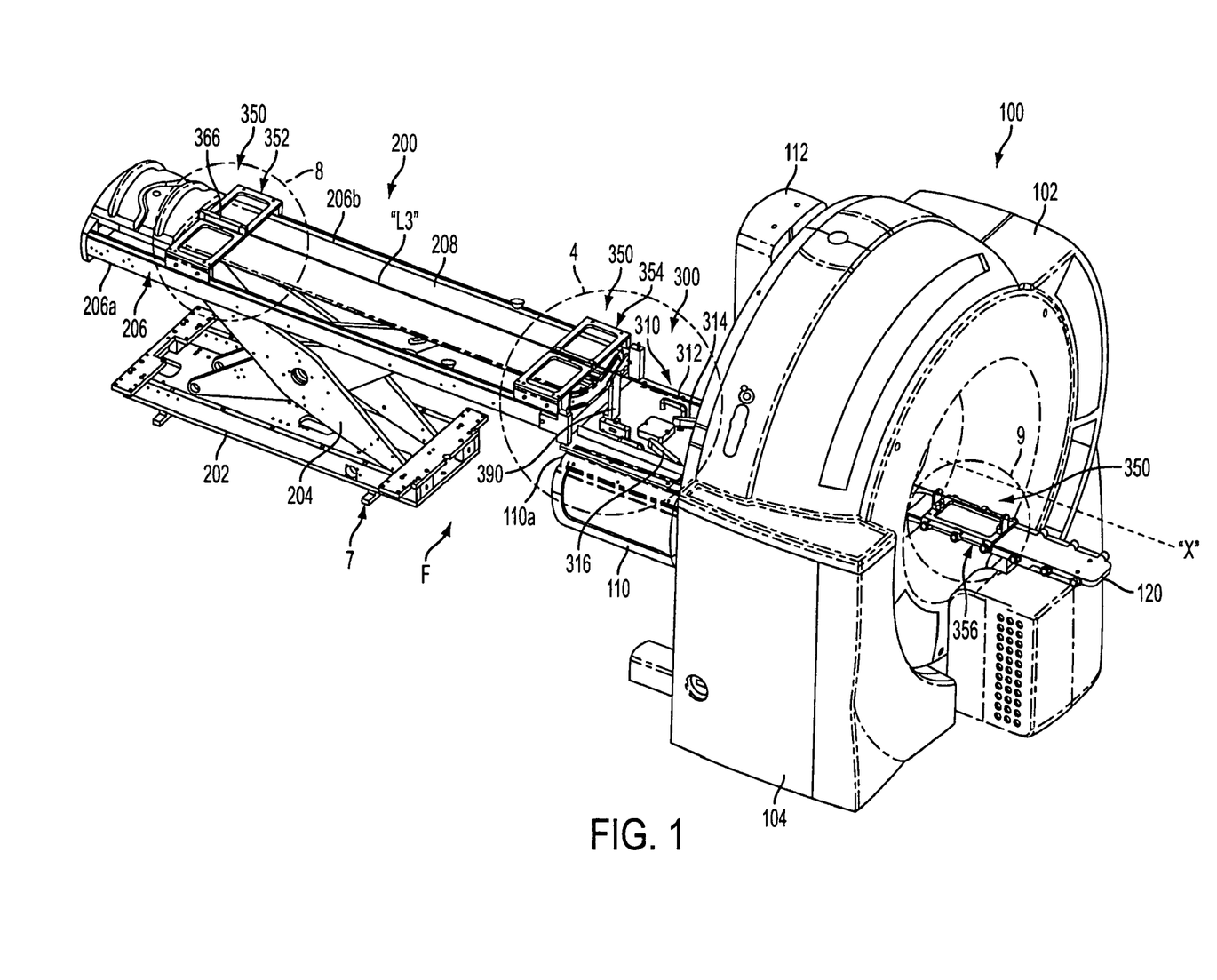
FIG. 1 is a perspective view of a nuclear imaging system including an alignment system in accordance with an embodiment of the present disclosure.

Referring now to the drawings, and first to FIG. 1, a nuclear medicine gantry 100 and patient handling system 200 are shown. Nuclear medicine gantry 100 includes a ring 102 operatively connected to and supported on a stand 104. Nuclear medicine gantry 100 further includes at least a first nuclear detector 110 and a second nuclear detector 112, each, operatively associated with and/or mounted to ring 102.

Patient handling system 200 includes a lower frame 202 supported on floor "F", a lift mechanism 204 operatively supported on lower frame 202, an upper frame 206 operatively supported on lift mechanism 204 and a patient bed or pallet 208 translatably supported on upper frame 206. Patient handling system 200 may be oriented such that patient bed 208 is translatable in directions parallel to a central axis of ring 102. Lift mechanism 204 (e.g., parallelogram style, scissors style, etc.) provides the up and down motion of upper frame 206 and patient bed 208 for patient loading and positioning.

As seen in FIGS. 1-12, in accordance with the present disclosure, an alignment system 300 is provided for properly and accurately aligning at least the first nuclear detector 110 with respect to an axis of rotation "X" of ring 102, and for aligning patient bed 208 with respect to the "X" axis of rotation of ring 102.

With reference to FIGS. 1-7, alignment system 300 includes a nuclear camera alignment fixture 310 selectively securable to a face 110a of nuclear detector 110. Nuclear camera alignment fixture 310 includes a plate 312 configured and dimensioned to at least partially overlie face 110a of nuclear detector 110. Nuclear camera alignment fixture 310 includes at least a pair of lasers 314, 316 mounted thereto or supported thereon. In particular, in one embodiment, magnetic strips 318a, 318b may be secured to plate 312 and each laser 314, 316 may be magnetically secured to a respective one of magnetic strips 318a, 318b. Each magnetic strip 318a, 318b may be recessed into a respective groove 319a, 319b formed in plate 312.

Figure 2:
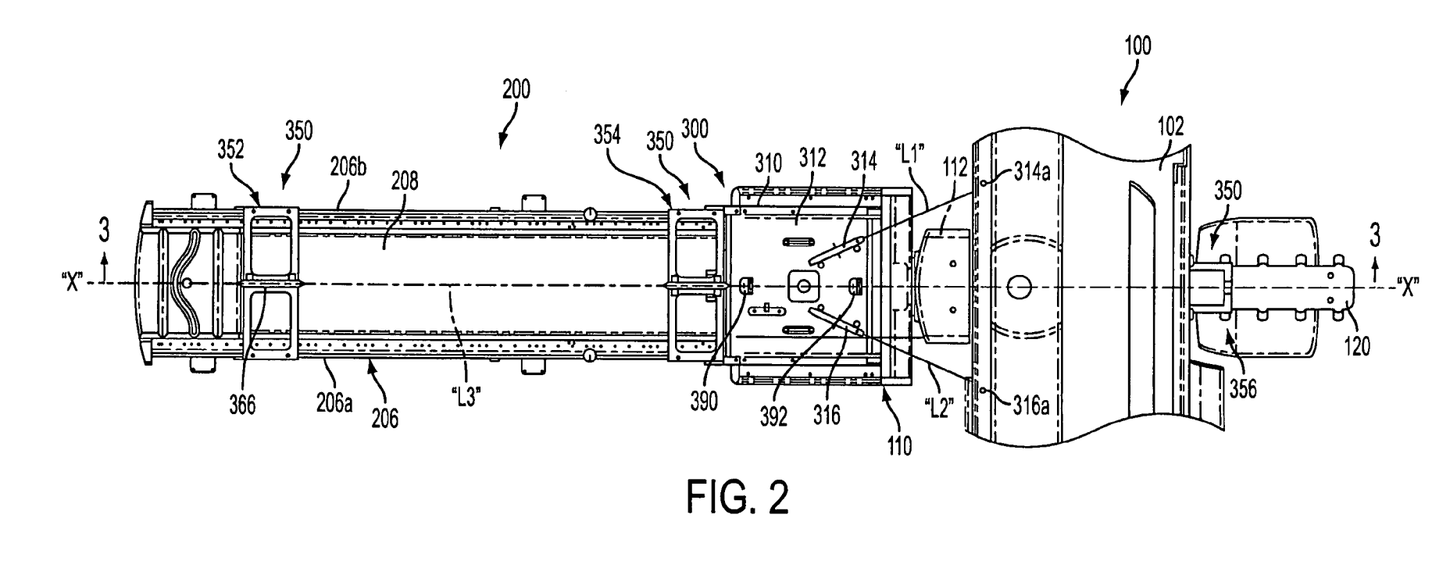
FIG. 2 is a top, plan view of the nuclear imaging system of FIG. 1.
Figure 5:
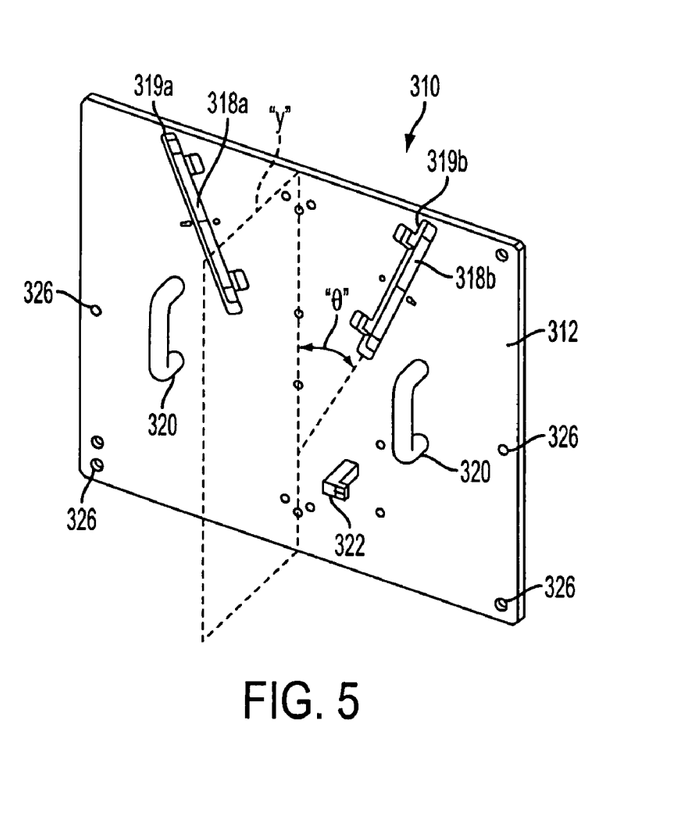
FIG. 5 is a top, perspective view of a nuclear camera alignment fixture of the alignment system of the present disclosure.

As seen in FIGS. 2 and 5, each laser 314, 316 is mounted to plate 312 at an angle "θ" with respect to a central orthogonal plane "Y" extending through plate 312. Lasers 314, 316 are mounted to plate 312 such that laser beams "L1, L2" thereof are emitted in diverging directions relative to one another. In this manner, as will be described in greater detail below, when plate 312 is mounted to face 110a of nuclear detector 110, lasers 314, 316 are oriented to direct respective laser beams "L1, L2" in the direction of ring 102.

Nuclear camera alignment fixture 310 may include at least one handle 320 for facilitating manipulation of plate 312 and lasers 314, 316 mounted thereto. Nuclear camera alignment fixture 310 may further include a clamping block 322 selectively securable to plate 312. Clamping block 322 may be used to secure a component or the like to plate 312.

Figure 6:
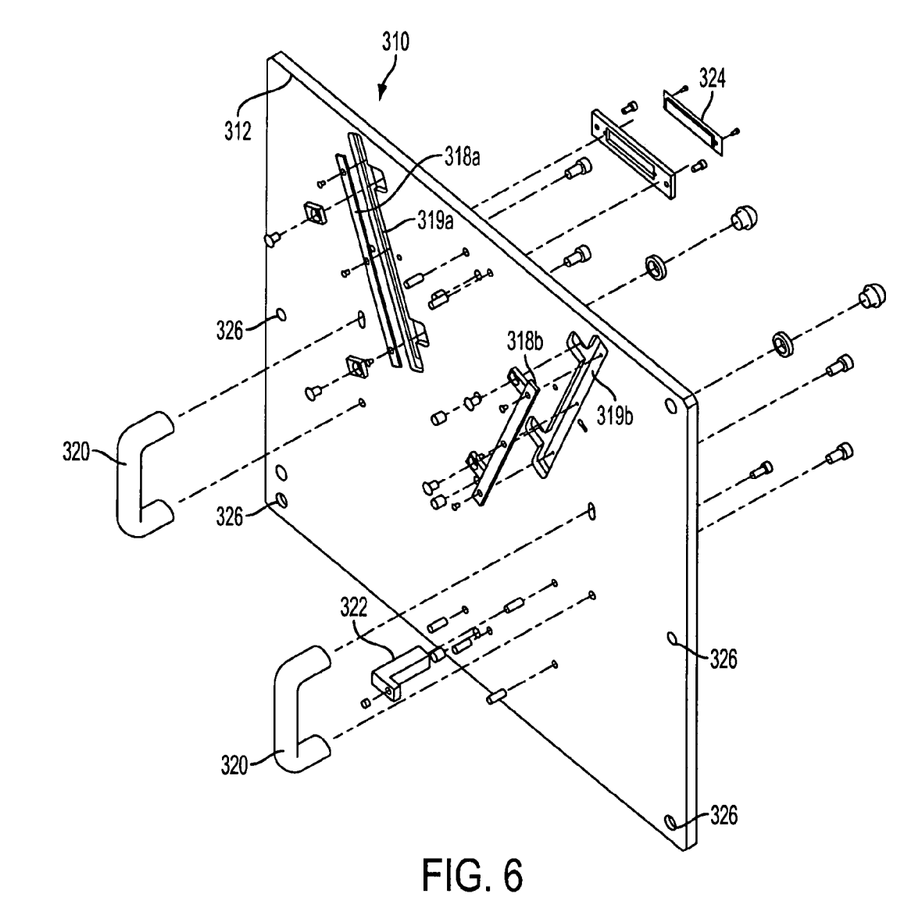
FIG. 6 is a bottom, perspective view of the nuclear camera alignment fixture of FIG. 5.
Figure 7:
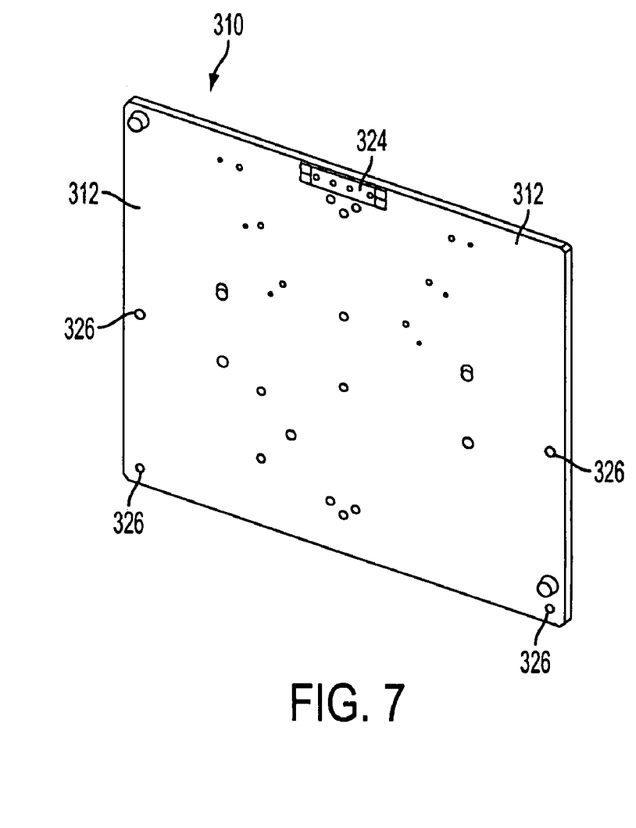
FIG. 7 is a top, perspective view, with parts separated, of the alignment plate of FIGS. 5 and 6.

As seen in FIGS. 6 and 7, nuclear camera alignment fixture 310 may include a collimator identification tag 324 secured to an underside thereof. Identification tag 324 may function to identify nuclear camera alignment fixture 310 for a particular nuclear detector 110.

Plate 312 includes a plurality of mounting holes 326 formed therein which correspond identically to mounting pins of nuclear detector 110 (not shown). Mounting holes 326 of plate 312 function to properly align and place nuclear camera alignment system 310 onto nuclear detector 110.

In accordance with the present disclosure, as seen in FIG. 2, nuclear camera alignment fixture 310 includes a pair of targets 314a, 316a provided on ring 102 of nuclear medicine gantry 100. Each target 314a, 316a may include and is not limited to a non-reflective surface, a crystal surface, a sensor and the like. Each target 314a, 316a is particularly located on ring 102 such that its location relative to the "X" axis of rotation of ring 102 is known. In particular, during the manufacture and/or assembly of nuclear medicine gantry 100, targets 314a, 316a are placed at known locations relative to the "X" axis of rotation. In so doing, targets 314a, 316a are used to accurately and properly align nuclear detector 110 with respect to the "X" axis of rotation, as will be discussed in greater detail below. By using targets 314a, 316a to align nuclear detector 110 relative to the "X" axis of rotation, nuclear detector 110 is aligned independently of and/or irrespective of the direction of gravity relative to nuclear medicine gantry 100 and the like.

In operation, in order to properly align nuclear detector 110 with ring 102 of nuclear medicine gantry 100, nuclear camera alignment fixture 310 is attached or mounted to face 110a of nuclear detector 110, in the manner described above. With nuclear camera alignment fixture 310 mounted to face 110a of nuclear detector 110, lasers 314 and 316 are activated to emit laser beams "L1, L2" therefrom. Nuclear detector 110 is then moved (i.e., moved in directions transverse/orthogonal to the "X" axis of rotation, and pivoted about an axis which is parallel to the "X" axis of rotation) until laser beams "L1, L2" hit their respective targets 314a, 316a. In other words, the movement of nuclear detector 110 is adjusted as needed until laser beams "L1, L2" hit respective targets 314a, 316a. In so doing, nuclear detector 110 is aligned with respect to the "X" axis of rotation of ring 102.

Turning now to FIGS. 1-4 and 8-12, alignment system 300 includes a patient handling system (PHS) alignment assembly 350 selectively securable to upper frame 206 of patient handling system 200. PHS alignment assembly 350 includes a pair of front PHS alignment fixtures 352, 354 selectively mounted to upper frame 206, wherein a first front alignment fixture 352 thereof is mounted to upper frame 206 at a location furthest from ring 102 and a second front alignment fixture 354 thereof is selectively mounted to upper frame 206 at a location closest to ring 102. PHS alignment assembly 350 further includes a rear PHS alignment fixture 356 supported on a mounting platform 120 of nuclear medicine gantry 100.

As best seen in FIGS. 1-4, 8 and 9, each of first and second front alignment fixtures 352, 354 of PHS alignment assembly 350 includes a pair of spaced apart legs 360, 362 for mounting onto respective rails 206a, 206b of upper frame 206, and plate 364 extending therebetween.

Figure 8:
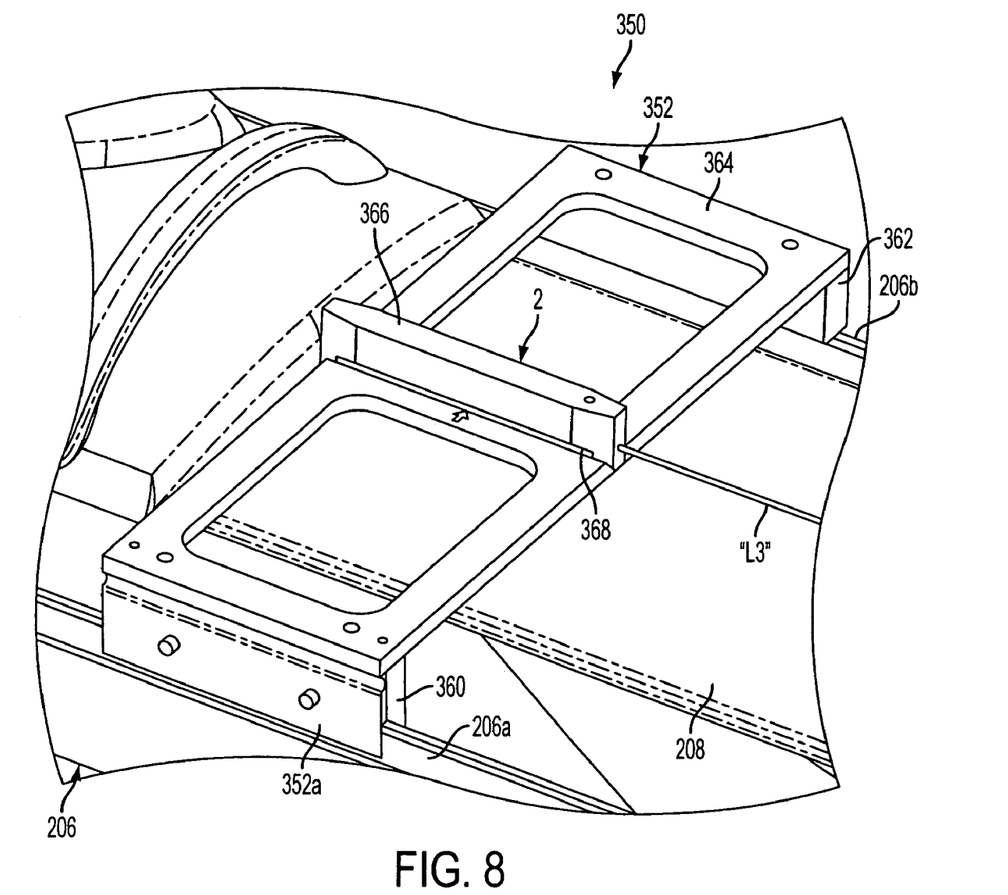
FIG. 8 is an enlarged view of the indicated area of detail of FIG. 1.

As seen in FIGS. 1 and 8, first front alignment fixture 352 of PHS alignment assembly 350 includes a laser 366 mounted to or supported on plate 364. Laser 366 is mounted on plate 364 such that a laser beam "L3" emitted therefrom travels in a direction substantially parallel to and/or co-linear with the "X" axis of rotation when first alignment fixture 352 is mounted to upper frame 206 of patient handling system 200. In one embodiment, a magnetic strip 368 may be secured to plate 364 such that laser 366 may be magnetically secured to magnetic strip 368.

Figure 4:
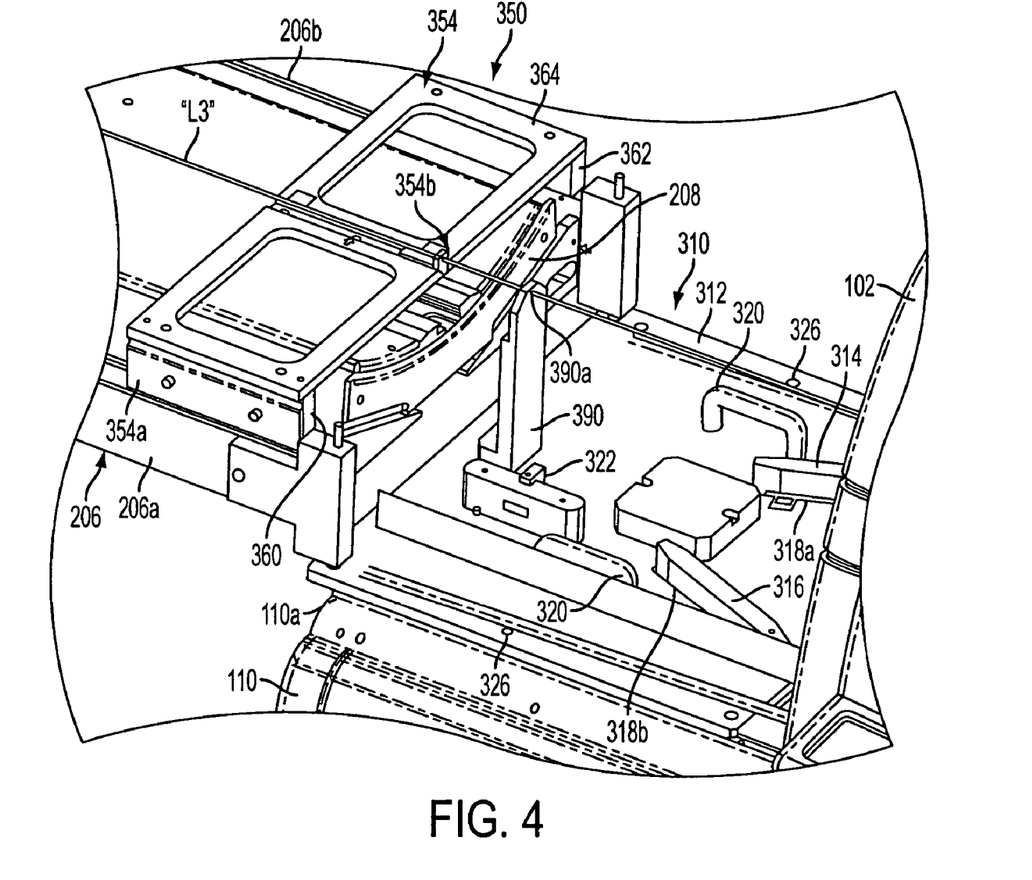
FIG. 4 is an enlarged view of the indicated area of detail of FIG. 1.

As seen in FIG. 4, second front alignment fixture 354 of PHS alignment assembly 350 includes an alignment site or target 354b. In operation, when first and second front alignment fixtures 352, 354 of PHS alignment assembly 350 are properly mounted to upper frame 206 and laser 366 activated to emit laser beam "L3" therefrom, laser beam "L3" passes through alignment site or target 354b of second front alignment fixture 354.

Figure 9:
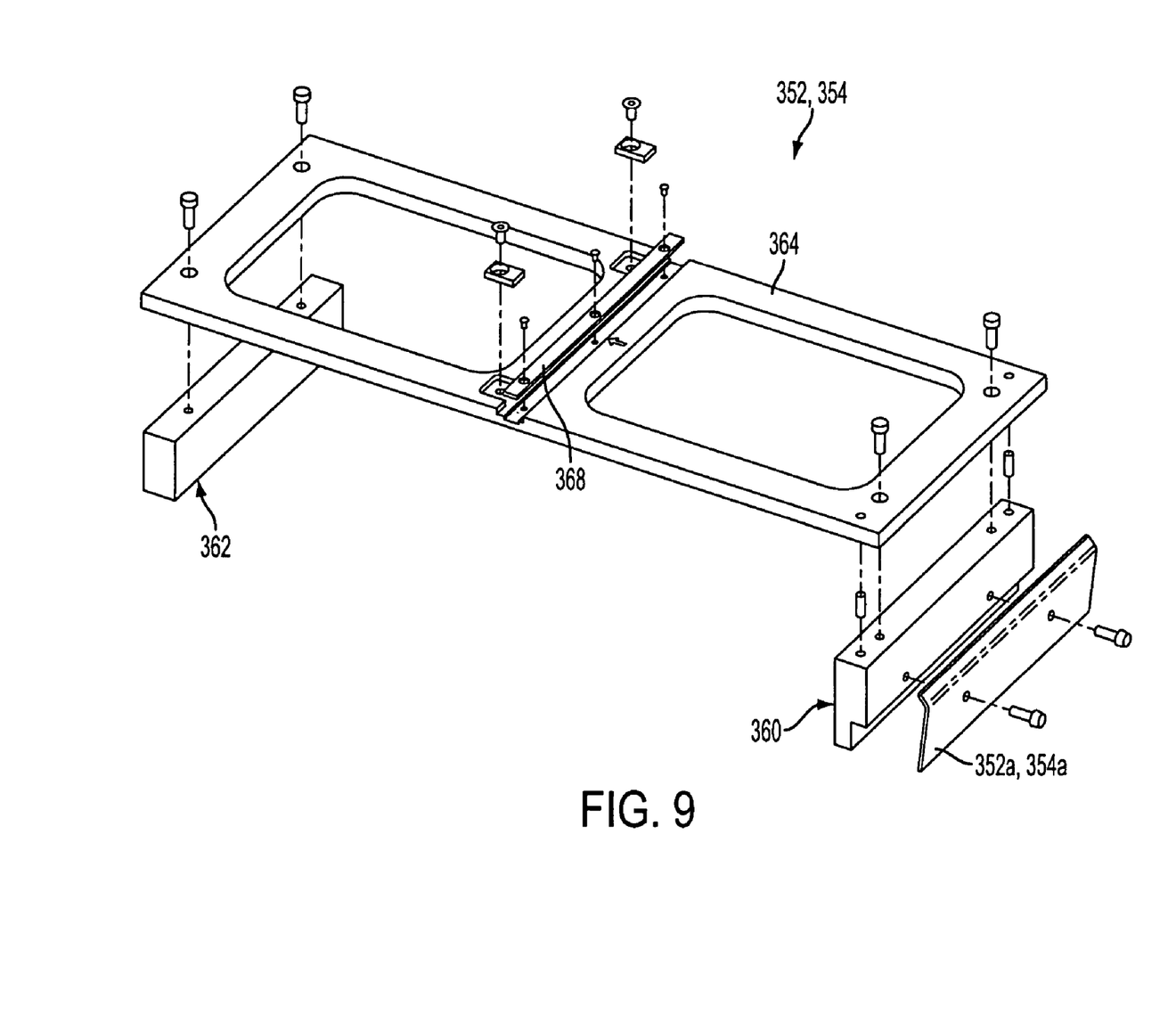
FIG. 9 is a perspective view of a patient handling system front alignment fixture of the patient handling system alignment assembly of the alignment system of the present disclosure.

Each of first and second front alignment fixtures 352, 354 of PHS alignment assembly 350 includes a respective clamp 352a, 354a configured and adapted to selectively clamp a respective one of first and second front alignment fixtures 352, 354 to rail 206a of upper frame 206.

In accordance with the present disclosure, alignment system 300 may include at least one, and as seen in FIGS. 1-4, at least a pair of alignment uprights 390, 392 selectively mountable to plate 312 of nuclear camera alignment fixture 310. Each alignment upright 390, 392 may be mounted to plate 312 of nuclear camera alignment fixture 310 such that alignment uprights 390, 392 are disposed within a plane extending through the "X" axis of rotation. Preferably, alignment uprights 390, 392 are disposed within a vertical plane extending through the "X" axis of rotation.

Each alignment upright 390, 392 defines a respective hole or passage 390a, 392a formed therein. Each passage 390a, 392a of alignment uprights 390, 392 is located at an identical vertical distance from a top surface of plate 312 of nuclear camera alignment fixture 310.

Referring now to FIGS. 1-3 and 10-12, PHS alignment assembly 350 of alignment system 300 further includes a rear PHS alignment fixture 356 supported on a mounting platform 120 operatively connected to ring 102 of nuclear medicine gantry 100.

Figure 3:
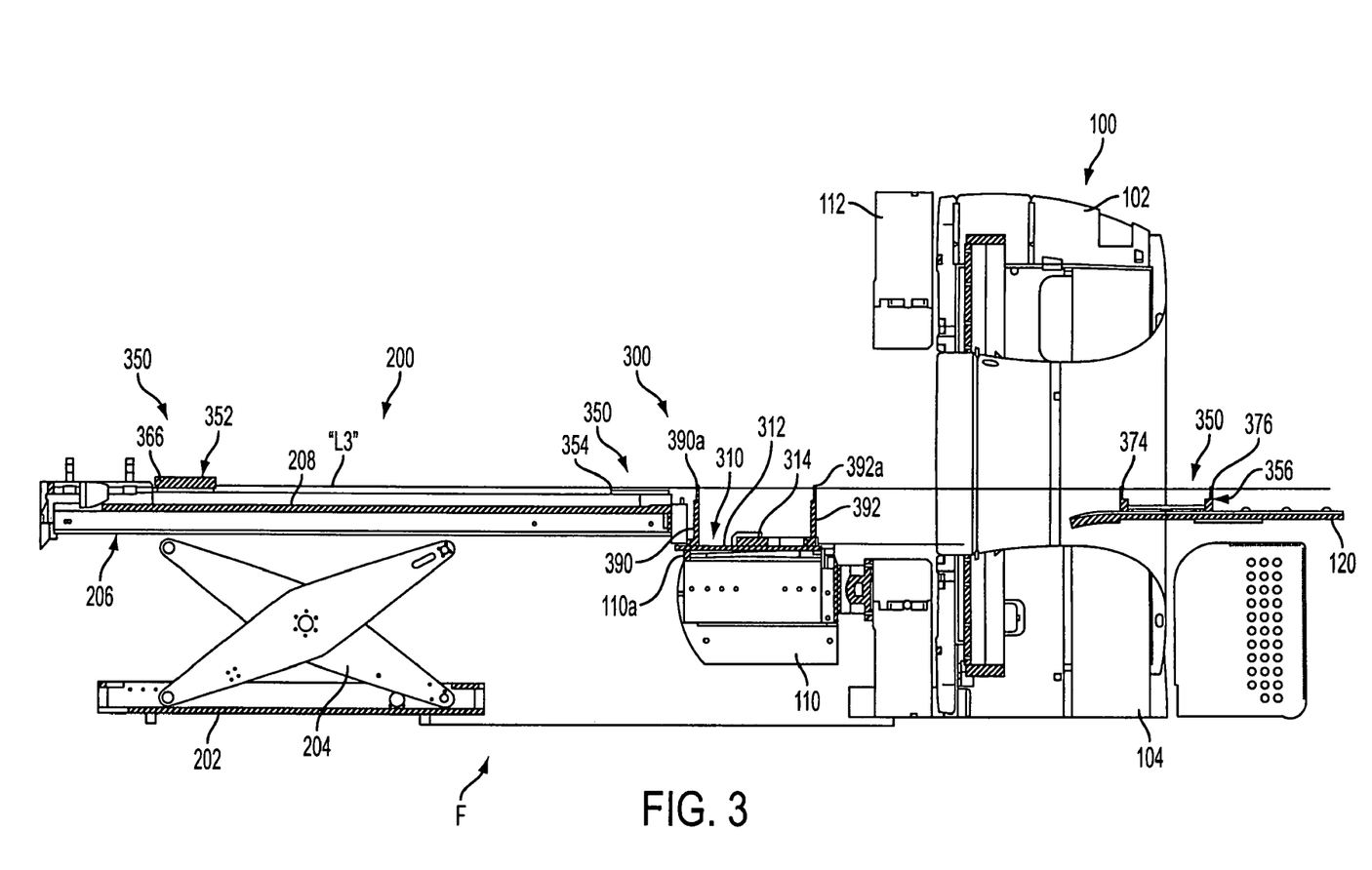
FIG. 3 is a longitudinal, cross-sectional view of the nuclear imaging system of FIGS. 1 and 2, as taken through 3-3 of FIG. 2.
Figure 10:
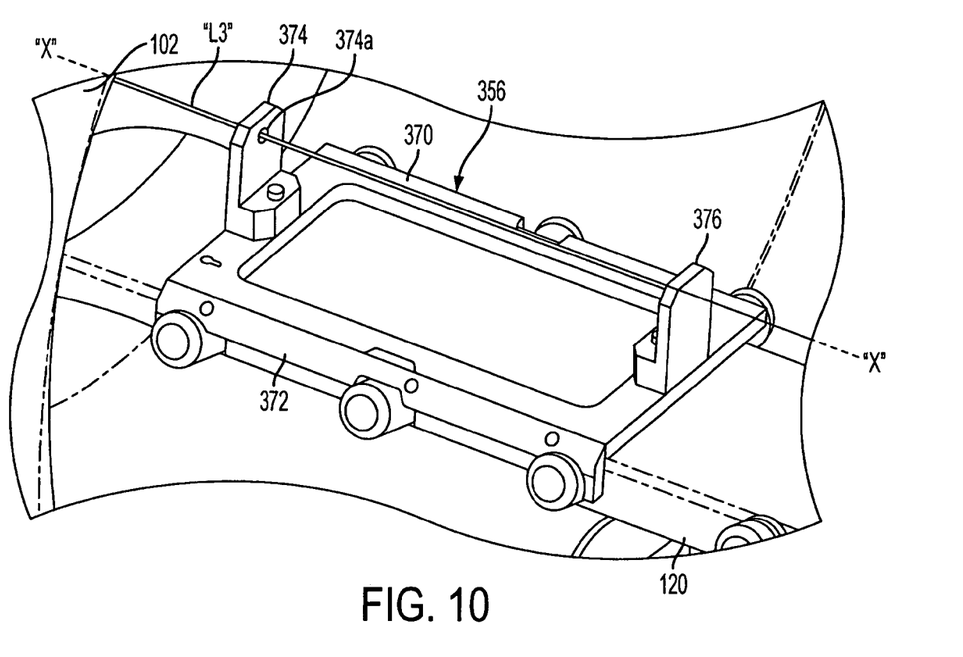
FIG. 10 is an enlarged view of the indicated area of detail of FIG. 1.
Figure 11:
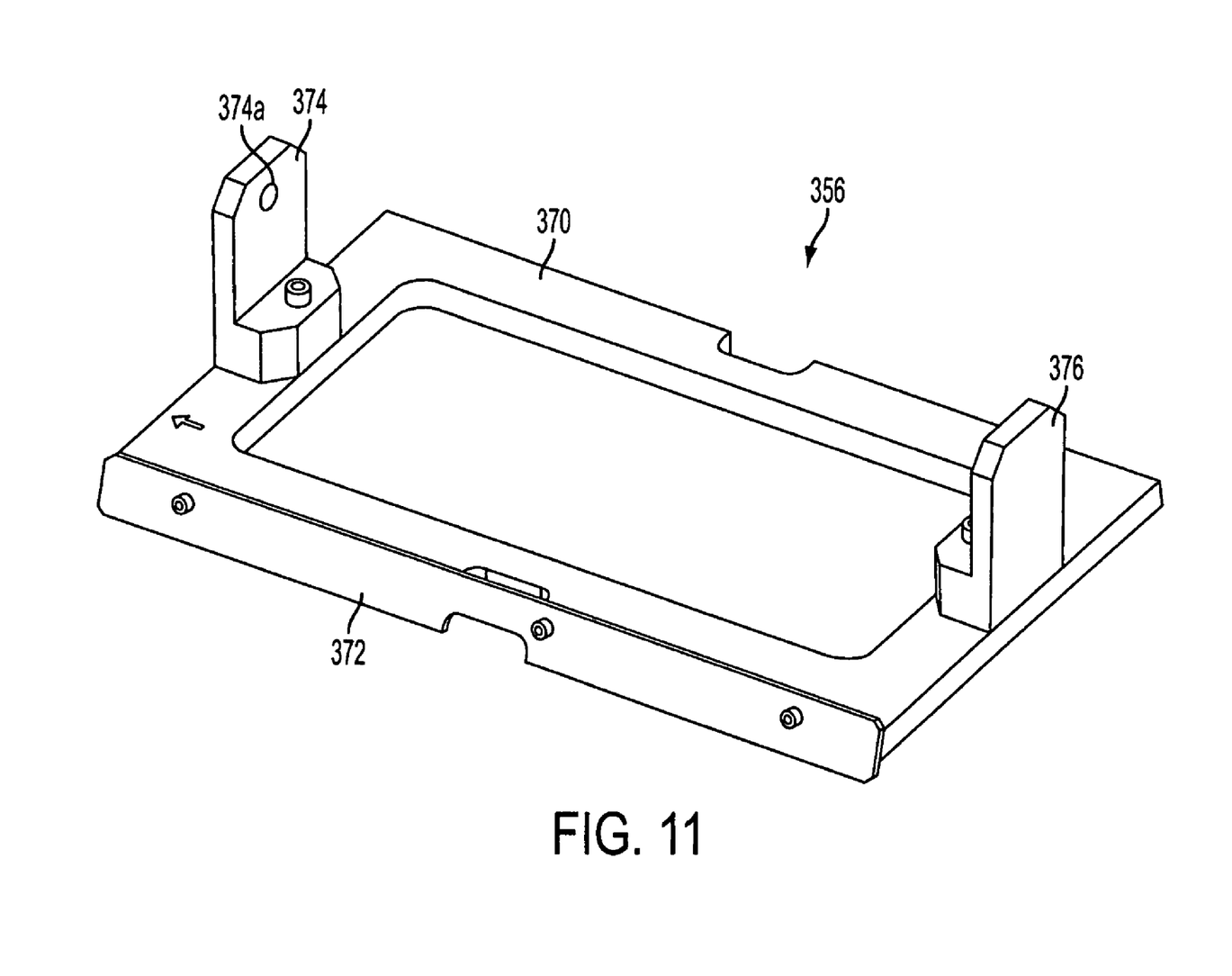
FIG. 11 is a top, perspective view of a patient handling system rear alignment fixture of the patient handling system alignment assembly of the alignment system of the present disclosure.
Figure 12:
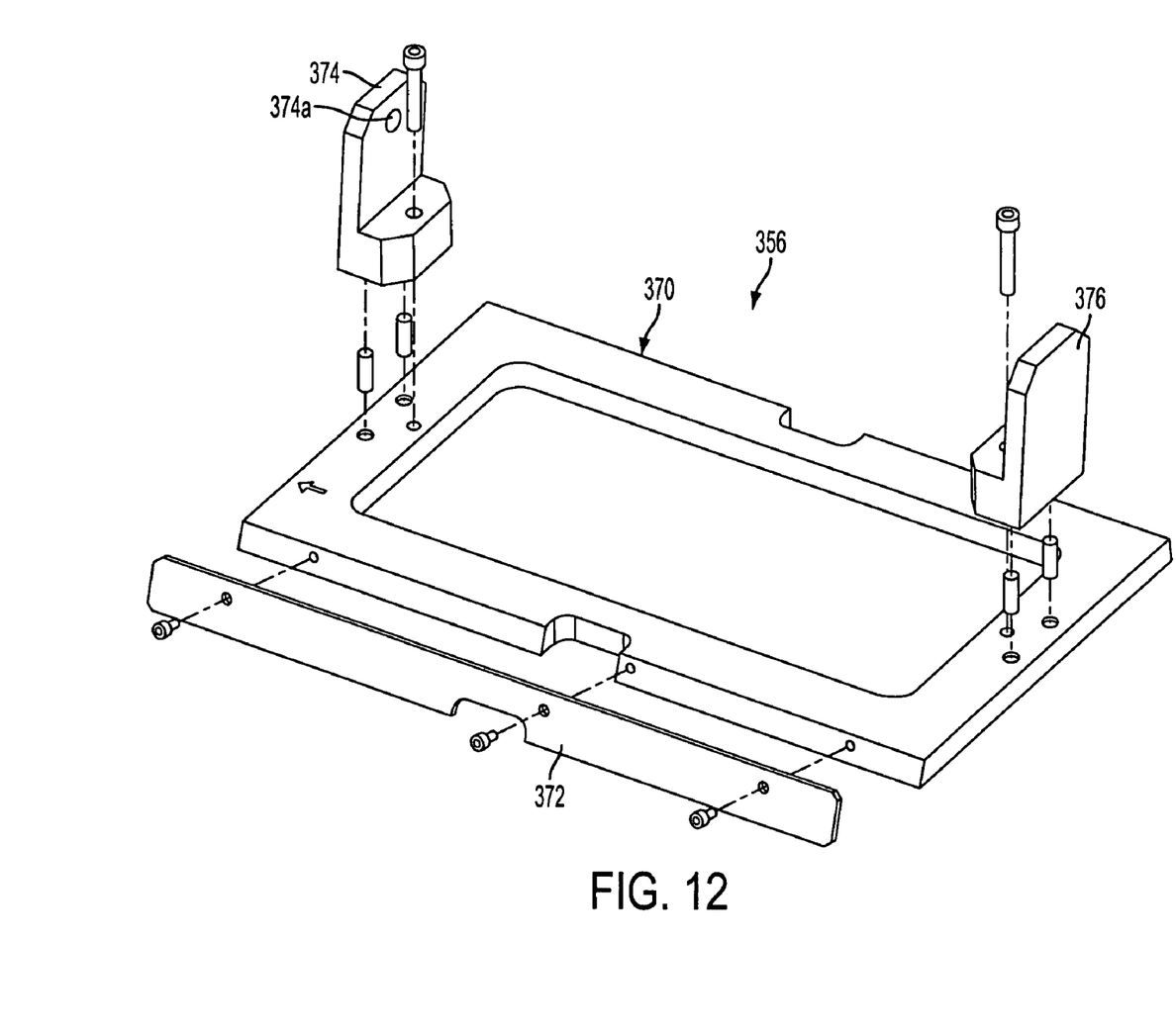
FIG. 12 is a top, perspective view, with parts separated, of the patient handling system rear alignment fixture of FIG. 11.

As seen in FIGS. 1-3, and in particular in FIGS. 10-12, rear PHS alignment fixture 356 includes a plate 370 selectively mountable to an upper surface of mounting platform 120 by a clamping plate 372. Rear PHS alignment fixture 356 further includes a pair of alignment uprights selectively mountable to plate 370. A first upright 374 is located in close proximity to patient handling system 200 when rear PHS alignment fixture 356 is mounted on mounting platform 120 and a second upright 376 is located in further proximity to patient handling system 200 when rear PHS alignment fixture 356 is mounted on mounting platform 120. First upright 374 and second upright 376 are located at juxtaposed ends of plate 370. First upright 374 includes an aperture 374a formed therethrough for passage of laser beam "L3" therethrough.

Aperture 374a of first upright 374 of rear PHS alignment fixture 356, when rear PHS alignment fixture 356 is mounted onto mounting platform 120, is located on the "X" axis of rotation.

In accordance with the present disclosure, alignment system 300 may include at least one, and as seen in FIGS. 1-4, at least a pair of alignment uprights 390, 392 selectively mountable to plate 312 of nuclear camera alignment fixture 310. Each alignment upright 390, 392 may be mounted to plate 312 of nuclear camera alignment fixture 310 such that alignment uprights 390, 392 are disposed within a plane extending through the "X" axis of rotation. Preferably, alignment uprights 390, 392 are disposed within a vertical plane extending through the "X" axis of rotation.

Each alignment upright 390, 392 defines a respective hole or passage 390a, 392a formed therein. Each passage 390a, 392a of alignment uprights 390, 392 is located at an identical vertical distance from a top surface of plate 312 of nuclear camera alignment fixture 310.

In operation, in order to align patient handling system 200 to the "X" axis of rotation, first front alignment fixture 352, second front alignment fixture 354, and rear PHS alignment fixture 356 are mounted to patient handling system 200 and nuclear medicine gantry 100, in the manner described above. With first front alignment fixture 352, second front alignment fixture 354, and rear PHS alignment fixture 356 so mounted, laser 366 is activated to shine laser beam "L3" from first front alignment fixture 352 toward rear PHS alignment fixture 356. Upper frame 206 is then raised or lowered, as needed, until laser beam "L3" shines through each passage 390a, 392a of alignment uprights 390, 392 and through aperture 374a of first upright 374 of rear PHS alignment fixture 356, onto second upright 376 of rear PHS alignment fixture 356.

It is envisioned and within the scope of the present disclosure for lasers 314, 316 and 366 to be fixedly and/or permanently supported on or in their respective locations within nuclear detector 110 and patient handling system 200. For example, first and second lasers 314, 316 may be mounted within nuclear detector 110, at a location, such that lasers 314, 316 may be used to hit targets "L1, L2" as described above in order to align nuclear detector 110 with respect to the "X" axis of rotation of ring 102. Additionally, third laser 366 may be mounted within patient bed 208 in order to align patient bed 208 with respect to the "X" axis of rotation of ring 102, in substantially the same manner as described above.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. An alignment system for use in connection with at least one of a patient handling system, and a nuclear medicine gantry defining an axis of rotation and having a nuclear detector operatively mounted thereto, the alignment system including:
   a nuclear camera alignment fixture selectively fixedly mountable to a face of the nuclear detector, the nuclear camera alignment fixture including a pair of lasers oriented substantially toward the nuclear medicine gantry, wherein each laser is capable of emitting a respective laser beam therefrom; and
   a pair of laser targets provided on the nuclear medicine gantry, each laser target having a fixed location with respect to the axis of rotation of the nuclear medicine gantry, wherein the nuclear detector is moved relative to the nuclear medicine gantry until each laser beam hits a respective laser target.

2. The alignment system according to claim 1, wherein the pair of lasers are divergent from one another.

3. The alignment system according to claim 1, wherein the nuclear camera alignment fixture includes a plate selectively mountable to the face of the nuclear detector, and wherein each laser is mounted to the plate thereof.

4. The alignment system according to claim 3, wherein the lasers are magnetically mounted to the plate.

5. The alignment system according to claim 3, wherein the lasers are oriented to transmit laser beams in a divergent direction relative to one another.

6. The alignment system according to claim 1, further comprising a patient handling system alignment assembly including:
   a first and a second front patient handling system alignment fixture each selectively mountable to the patient handling system;
   a rear patient handling system alignment fixture selectively mountable to a mounting platform of the nuclear medicine gantry; and
   a laser supported on the first front patient handling system alignment fixture and oriented to emit a laser beam in the direction of the nuclear medicine gantry, wherein a height of the patient handling system is adjusted until the laser beam of the first front patient handling system alignment fixture hits a target of the rear patient handling system alignment fixture.

7. The alignment system according to claim 6, wherein the first front patient handling system alignment fixture is mounted to the patient handling system at a location remote from the nuclear medicine gantry, and wherein the second front patient handling system alignment fixture is mounted to the patient handling system at a location proximate to the nuclear medicine gantry.

8. The alignment system according to claim 7, wherein the second front patient handling system alignment fixture includes a target supported thereon, wherein the laser beam emitted by the laser of the first front patient handling system is directed through the target of the second front patient handling system alignment fixture.

9. The alignment system according to claim 8, wherein the rear patient handling system alignment fixture includes a pair of uprights extending therefrom, wherein a first of the pair of uprights includes an aperture through which the laser beam emitted by the laser of the first front patient handling system is directed through and a second of the pair of uprights includes a target.

10. The alignment system according to claim 9, further comprising a pair of uprights mounted to the nuclear camera alignment fixture, wherein each upright of the nuclear camera alignment fixture includes an aperture formed near a distal end thereof, wherein the laser beam emitted by the laser of the first front patient handling system is directed through each of the apertures of the pair of uprights of the nuclear camera alignment fixture.

11. The alignment system according to claim 10, wherein the patient handling system is adjusted such that the laser beam emitted by the laser of the first front patient handling system is directed through each of the apertures of the pair of uprights of the nuclear camera alignment fixture.

12. The alignment system according to claim 11, wherein the pair of uprights of the nuclear camera alignment fixture are in a plane defined by the axis of rotation of the nuclear medicine gantry.

13. The alignment system according to claim 6, wherein the nuclear camera alignment fixture includes a plate selectively mountable to the face of the nuclear detector, and wherein each of the pair of lasers is mounted to the plate thereof.

14. The alignment system according to claim 13, wherein each of the pair of lasers of the nuclear camera alignment fixture is magnetically mounted to the plate thereof.

15. The alignment system according to claim 13, wherein each of the pair of lasers of the nuclear camera alignment fixture is oriented to transmit laser beams in a divergent direction relative to one another.

16. An alignment system for use in connection with at least one of a patient handling system, and a nuclear medicine gantry defining an axis of rotation and having a nuclear detector operatively mounted thereto, the alignment system including:
 a nuclear camera alignment fixture selectively fixedly mountable to a face of the nuclear detector, the nuclear camera alignment fixture including:
  a pair of lasers oriented substantially toward the nuclear medicine gantry, each laser is capable of emitting a respective laser beam therefrom; and
  a pair of laser targets provided on the nuclear medicine gantry, each laser target having a fixed location with respect to the axis of rotation of the nuclear medicine gantry, wherein the nuclear camera is moved relative to the nuclear medicine gantry until each laser beam hits a respective laser target; and
 a patient handling system alignment assembly including:
  a first and a second front patient handling system alignment fixture each selectively mountable to the patient handling system;
  a rear patient handling system alignment fixture selectively mountable to a mounting platform of the nuclear medicine gantry; and
  a laser supported on the first front patient handling system alignment fixture and oriented to emit a laser beam in the direction of the nuclear medicine gantry, wherein a height of the patient handling system is adjusted until the laser beam of the first front patient handling system alignment fixture hits a target of the rear patient handling system alignment fixture.

17. A method of aligning a nuclear detector of a nuclear medicine gantry and a patient handling system each to an axis of rotation of the nuclear medicine gantry, the method comprising the steps of:
 mounting a pair of lasers to the nuclear detector, wherein the pair of lasers are located in a known position relative to a center of the nuclear detector and substantially directed toward the nuclear medicine gantry;
 emitting laser beams from each of the pair of lasers in the direction of the nuclear medicine gantry;
 moving the nuclear detector relative to a ring of the nuclear medicine gantry until each laser beam hits a respective target provided on the nuclear medicine gantry, wherein each target is located at a known position relative to the axis of rotation of the nuclear medicine gantry;
 mounting a laser to the patient handling system, wherein the laser of the patient handling system is directed toward the nuclear medicine gantry;
 emitting a laser beam from the laser of the patient handling system in the direction of the nuclear medicine gantry; and
 moving the patient handling system until the laser beam thereof is aligned with the axis of rotation of the nuclear medicine gantry.

18. The method according to claim 17, further comprising the step of emitting the laser beam of the laser of the patient handling system through at least one upright provided on the nuclear detector.

19. The method according to claim 18, further comprising the steps of:
 placing the laser of the patient handling system at a location remote relative to the nuclear medicine gantry; and
 emitting the laser beam of the laser of the patient handling system through a target provided on the patient handling system at a location in close proximity to the nuclear medicine gantry.

* * * * *